United States Patent [19]

Fechner et al.

[11] Patent Number: 5,286,494
[45] Date of Patent: Feb. 15, 1994

[54] MEDICINAL AGENTS WITH SUSTAINED ACTION

[75] Inventors: Christian Fechner; Michael Hümpel; Fred Windt-Hanke; Johannes Tack, all of Berlin, Fed. Rep. of Germany

[73] Assignee: Schering Aktiengesellschaft, Berlin and Bergkamen, Fed. Rep. of Germany

[21] Appl. No.: 715,699

[22] Filed: Jun. 17, 1991

Related U.S. Application Data

[63] Continuation of Ser. No. 394,999, Aug. 17, 1989, abandoned, which is a continuation of Ser. No. 165,197, Apr. 25, 1988, abandoned.

[30] Foreign Application Priority Data

Jul. 2, 1986 [DE] Fed. Rep. of Germany ....... 3622487

[51] Int. Cl.$^5$ .......................... A61K 9/16; A61K 9/54
[52] U.S. Cl. ..................... 424/490; 424/489; 424/493; 424/494; 424/497; 424/499; 514/822
[58] Field of Search ............. 424/490, 494, 497, 493, 424/489

[56] References Cited

U.S. PATENT DOCUMENTS

| | | | |
|---|---|---|---|
| 3,835,221 | 9/1974 | Fulberth et al. | 424/458 |
| 3,854,480 | 12/1974 | Zaffaroni | 424/424 |
| 4,192,891 | 3/1980 | Haslanger | 514/573 X |
| 4,193,926 | 3/1980 | Schmiechen et al. | 548/527 X |
| 4,193,985 | 3/1980 | Bechgaard | 424/459 |
| 4,264,574 | 4/1981 | Cherqui et al. | 424/497 |
| 4,600,577 | 7/1986 | Didriksen | 424/462 |
| 4,663,150 | 5/1987 | Panoz et al. | 424/497 |
| 4,687,660 | 8/1987 | Baker et al. | 424/473 |
| 4,755,180 | 7/1988 | Ayer et al. | 424/473 |
| 4,800,084 | 1/1989 | Zerbe | 424/458 |
| 4,867,984 | 9/1989 | Patel | 424/497 |
| 4,891,230 | 1/1990 | Geoghegan et al. | 424/497 |

FOREIGN PATENT DOCUMENTS

| | | |
|---|---|---|
| 0107557 | 5/1984 | European Pat. Off. |
| 0142561 | 5/1985 | European Pat. Off. |
| 0153105 | 8/1985 | European Pat. Off. |

OTHER PUBLICATIONS

Merck Index, pp. 1040-1042.
Fries et al., "Aufbau von Pellets mit Hilfe eines Kugelcoaters." Pharm. Ind. 48, Nr. 2 (1986), pp. 187-192.
Merck Index, pp. 249, 1051.
Thiel et al., "Fluidized bed film coating of an ordered powder mixture to produce microencapsulated ordered units," J. Pharm Pharmacol. 1984, 36: 145-152, 1984.
The Merck Index, 11th edition, 1989, p. 1180.
Deasey, Microencapsulation and related Drug Processes, Marcel Decker, Inc., New York, 1984, pp.21, 22, 149.

Primary Examiner—Thurman K. Page
Assistant Examiner—James M. Spear
Attorney, Agent, or Firm—Millen, White, Zelano & Branigan

[57] ABSTRACT

Medicinal agents are claimed exhibiting sustained release of active compound, containing a solid active ingredient, poorly soluble in water, and auxiliary agents, characterized in that the active compound, in a microcrystalline form or in form of a molecular dispersion, is distributed in or on pellets, and that the pellets are covered by a membrane having retarded permeability with respect to the active compound.

11 Claims, No Drawings

MEDICINAL AGENTS WITH SUSTAINED ACTION

This application is a continuation of application Ser. No. 07/394,999, filed Aug. 17, 1989 abandoned, which is a continuation of application Ser. No. 07/165,197, filed Apr. 25, 1988, abandoned.

The invention relates to medicinal agents with sustained release of active compound, containing a solid active ingredient, poorly soluble in water, and auxiliary agents, as well as to a process for the production thereof.

It is known that it is usually very problematical to produce, from solid active agents having poor water solubility, medicinal agents providing retarded release of the active ingredient in sufficient quantity. The medicinal agents of this invention are designed so that they generally release the active ingredient in adequate amounts over a sufficiently long time interval. They are characterized in that the active agent is distributed in or on pellets in microcrystalline form or in molecular dispersion, and that the pellets are covered with a diffusion membrane with a permeability having retarding action for the active ingredient.

The pellets preferably have an average diameter of 0.3–3.0 mm and, in particular, a diameter of 0.7–1.4 mm. The thickness of the membrane covering the pellets is dependent on the permeability for the active ingredient, normally amounting to 0.01–0.5 mm and, in particular, 0.04–0.20 mm.

The pellets contain as auxiliary agents essentially the customary pharmacologically acceptable fillers and auxiliary media. Suitable fillers are, for example, sugar alcohols, such as mannitol, monosaccharides, such as glucose, fructose or galactose, disaccharides, such as sucrose or lactose, polysaccharides, such as amylose, starch or cellulose, chemically modified polysaccharides, such as methylcellulose, inorganic fillers, such as magnesium oxide, talc, disperse silicic acid, magnesium stearate, etc.

Auxiliary agents that can be mentioned are, for example, the binders customarily employed in galenic pharmacy, such as starch, starch syrup, microcrystalline cellulose (e.g. "Avicel" - Lehman u. Voss u. Co., D-Hamburg), carboxymethylcellulose, alginates, or polyvinylpyrrolidone.

In addition to the aforementioned auxiliary agents, the pellets can contain further auxiliary agents such as colorants, flavoring agents, plasticizers, etc.

These auxiliary agents either are mixed with the microcrystalline active compound having an average grain size of maximally 0.1 mm and processed into pellets with the addition of water in a manner well known to one skilled in the art, or pellets devoid of active compound are sprayed with a solution of the active compound in a readily volatile solvent (such as dichloromethane, methanol, ethanol, isopropanol, or mixtures of these solvents), thus obtaining pellets covered with a layer of the active ingredient, in the form of a molecular dispersion or in microcrystalline form, having a particle size of maximally 0.1 mm.

In order to reach adequate dissolution rates, the active compound should normally exhibit a surface area value of at least 20,000 cm$^2$ per g. In cases of extremely low water solubility, it is advantageous to utilize the active compound in a molecular-dispersion distribution. This can be achieved, for example, by recrystallizing the active compound from an organic solution with suitable agents of polyethylene glycol (for example, PEG 6000).

The thus-produced pellets are covered according to this invention with a membrane exhibiting retarded permeability for the active compound and being insoluble in the gastrointestinal tract. The following pharmacologically acceptable polymers can be utilized, for example for producing the membrane:

Acrylic acid esters, methacrylic acid esters, copolymers of acrylic and methacrylic acid esters, vinyl acetates, modified cellulose derivatives, and so forth.

Especially suitable polymers for producing the membrane are, inter alia, copolymers of methacrylic acid and methacrylic acid esters with a variably adjustable content of quaternary ammonium groups which latter determine the extent of hydrophilic property and thus also permeability of the polymers.

Typical representatives of this class of compounds are, for example, the acrylic resins "Eudragit"-RL and "Eudragit"-RS sold by the company Röhm-Pharma. These polymers exhibit an ammonium group ratio of about 1:20 ("Eudragit"-RL) and about 1:40 ("Eudragit"-RS)—molar ratio of ammonium groups to neutral acrylic acid esters. The permeability of the "Eudragit"-RL/RS membrane can be arbitrarily set by means of the mixing ratio of the components. The mixing ratio required for a desired rate of release is to be determined conventionally for the individual active compounds; it ranges ordinarily within the limits of 20:80% by weight to 80:20% by weight of "Eudragit"-RL:"Eudragit"-RS. The permeability of the diffusion membrane can be additionally influenced further by adding plasticizing agents (e.g. "Carbowax", triacetin, etc.) and perhaps additional auxiliary agents, such as talc or magnesium stearate as abherents and smoothing agents. Additionally, for improving coloration, it is possible to add to the polymers, for example, titanium dioxide or colored pigments, such as iron oxide pigments, which likewise exert a certain influence on the permeability of the diffusion membrane.

The pellets are sprayed, for example, with a solution of the polymer in a readily volatile solvent (such as dichloromethane, methanol, ethanol, isopropanol, or mixtures of these solvents). The rate of release of active agent can be varied as desired within wide limits by the choice of suitable polymers and additives, by selection of the quantity thereof, and thus of the thickness of the diffusion membrane, and by choosing the desired grain size of the active ingredient. Selection of the optimum parameters must in each case be determined in preliminary tests, as they are sufficiently known to those skilled in the art.

The pellets can be pressed conventionally into tablets or dragees, if desired, or they can be filled into suitable capsules, such as those of hard gelatin.

Active compounds of poor water solubility included in the following active agent groups are suitable, for example, for producing the medicinal agents according to this invention:

Steroid hormones having gestagen activity, such as, for example, 13-ethyl-17$\beta$-hydroxy-18,19-dinor-17$\alpha$-pregn-4-en-20-yl-3-one (=levonorgestrel), 13-ethyl-17$\beta$-hydroxy-18,19-dinor-17$\alpha$-pregna-1,4-dion-20-yn-3-one (=gestodene) or 13-ethyl-17$\beta$-hydroxy-11-methylene-18,19-dinor-17$\alpha$-pregn-4-en-20-yne (desorgestrel), steroid hormones having estrogen activity, such as 3-hydroxy-1,3,5(10)-estratrien-17-one (=estrene) or 1,9-nor-17α-pregna-1,3,5(10)-trien-20-yne-3,17β-diol (ethynylestradiol).

Steroid hormones having androgen activity, such as 17β-hydroxy-4-androsten-3-one (=testosterone) and its esters, or 17β-hydroxy-1α-methyl-5α-androsten-3-one (=mesterolone).

Steroid hormones having antiandrogen activity, such as 17α-acetoxy-6-chloro-1β,2β-dihydro-3'H-cyclopropa[1,2]pregna-1,4,6-triene-3,20-dione (cyproterone acetate).

Corticoids, such as 11β,17α,21-trihydroxy-4-pregnene-3,20-dione (=hydrocortisone), 11β,17α,21-trihydroxy-1,4-pregnadiene-3,20-dione (=prednisolone), 11β,17α,21-trihydroxy-6α-methyl-1,4-pregnatriene-3,20-dione (=methylprednisolone), and 6α-fluoro-11β,21-dihydroxy-16α-methyl-1,4-pregnadiene-3,20-dione (=difluocortolone).

Ergolines, such as 3-(9,10-dihydro-6-methyl-8α-ergolinyl)-1,1-diethylurea (=ergoline), 3-(2-bromo-9,10-dihydro-6-methyl-8α-ergolinyl)-1,1-diethylurea (=bromoergoline) or 3-(6-methyl-8α-ergolinyl)-1,1-diethylurea (=terguride).

Antihypertonic agents, such as 7α-acetylthio17α-hydroxy-3-oxo-4-pregnene-21-carboxylic acid γ-lactone (=spironolactone) or 7α-acetylthio-15β,16β-methylene-3-oxo-17α-pregna-1,4-diene-21,17-carbolactone (=mespirenone).

Anticoagulants, such as 5-[hexahydro-5-hydroxy-4-(3-hydroxy-4-methyl-1-octen-6-ynyl)-2(1H)-pentalenylidene]pentanoic acid (=iloprost).

Psychopharmaceuticals, such as 4-(3-cyclopentyloxy-4-methoxyphenyl)-2-pyrrolidone (=rolipram).

The actual examples set out below serve for providing a more detailed description of the invention.

EXAMPLE 1

(a) 7.2 kg of neutral pellets having a grain size from 1.1 to 1.2 mm, "Placebo Pellets" of the Werner company, D-2082 Tornesch, are sprayed, in a suitable coating pan, with a solution of 0.18 kg of 4-(3-cyclopentyloxy-4-methoxyphenyl)-2-pyrrolidone (=rolipram)
0.816 kg of dichloromethane and
0.294 kg of methanol.

The spray-coating step is performed by means of an ultrasonic spray nozzle or a compressed-air atomizer while the pan revolves slowly in a warm air stream.

(b) 1.0 kg of pellets containing active compound, prepared according to Example 1(a), are sprayed with a solution of 0.10 kg of "Eudragit"-RL and
0.40 kg of "Eudragit"-RS in
0.665 kg of dichloromethane and
0.285 kg of isopropyl alcohol.

The spray-coating process takes place in a fluidized-bed granulator.

The thus-obtained timed-release pellets exhibit the following composition:

| | |
|---|---|
| 19.56 mg | of rolipram |
| 944.48 mg | of proportion of neutral pellets |
| 7.26 mg | of "Eudragit"-RL |
| 28.20 mg | of "Eudragit"-RS |
| 1,000.00 mg | |

The in-vitro release test made on a separated dose of 4.78 mg of rolipram according to USP XXI in phosphate buffer solution, pH 7.3, resulted in the following values:

| After 2 Hours | After 4 Hours | After 8 Hours |
|---|---|---|
| 11.9% | 31.7% | 66.8% of dose |

EXAMPLE 2

(a)
0.779 kg of lactose, DIN 30
0.195 kg of "Avicel" PH 101 and
0.025 kg of 4-(3-cyclopentyloxy-4-methoxyphenyl)-2-pyrrolidone (=rolipram), micro 20, are screened to 0.315 mm and mixed homogeneously. The powder mixture is thoroughly moistened with 0.43 kg of water, passed through a suitable perforated disk granulating unit so that rough granules are produced having an extruded diameter of about 1.0 mm and an extruded length of about 4–10 mm. The rough granules are rounded to pellets and dried.

(b)
0.3 kg of pellets containing active compound, according to Example 2(a), are sprayed with a solution of 0.01 kg of "Eudragit"-RL and
0.04 kg of "Eudragit"-RS in
0.665 kg of dichloromethane and
0.285 kg of isopropanol.

The spraying process takes place in a fluidized-bed granulator.

The thus-obtained timed-release pellets exhibit the following composition:

| | |
|---|---|
| 23.90 mg | of rolipram |
| 744.75 mg | of lactose |
| 186.40 mg | of "Avicel" |
| 9.00 mg | of "Eudragit"-RL |
| 35.96 mg | of "Eudragit"-RS |
| 1,000.00 mg | |

The in-vitro release test of a separated dose of 4.78 mg of rolipram according to USP XXI in phosphate buffer solution, pH 7.3, yielded the following values:

| After 2 Hours | After 4 Hours | After 8 Hours |
|---|---|---|
| 3.7% | 8.4% | 18.9% of dose |

(c) For producing the special medicines, respectively 200 mg of pellets are filled into rigid gelatin capsules.

EXAMPLE 3

(a)
0.800 kg of lactose, DIN 30
0.200 kg of "Avicel" PH 101
0.033 kg of β-cyclodextrin and
0.0012 kg of 5-[hexahydro-5-hydroxy-4-(3-hydroxy-4-methyl-1-octen-6-ynyl)-2(1H)-pentalenylidene]pentanoic acid (=iloprost) are screened and mixed homogeneously. The powder mixture is thoroughly moistened with 0.362 kg of water, passed through a suitable perforated disk granulating unit so that rough granules are produced having a rod diameter of about 1.0–1.5 mm and a rod length of about 4–10 mm. The rough granules are rounded into pellets and dried.

(b)

0.300 kg of pellets containing active compound in accordance with Example 3(a) are sprayed with a solution of 0.010 kg of "Eudragit"-RL and
0.040 kg of "Eudragit"-RS in
0.665 kg of dichloromethane and
0.285 kg of isopropanol.

The spraying step takes place in a fluidized-bed granulator.

The thus-prepared timed-release pellets contain, per gram, 0.97 mg of iloprost.

The in-vitro release of a separated dose of 0.3 mg of iloprost according to USP XXI in phosphate buufer solution, pH 7.5, resulted in the following values:

| Time (Hours) | Cumulative Release in % |
|---|---|
| 1 | 57.1% |
| 2 | 99.6% |
| 3 | 99.6% |
| 6 | 103.5% |
| 8 | 99.1% |

EXAMPLE 4

(a)

0.800 kg of lactose, DIN 30
0.200 kg of "Avicel" PH 101
0.033 kg of $\beta$-cyclodextrin
0.0012 kg of 5-[hexahydro-5-hydroxy-4-(3-hydroxy-4-methyl-1-octen-6-ynyl)-2(1H)-pentalenylidene]pentanoic acid (=iloprost) are screened and mixed homogeneously. The powder mixture is thoroughly moistened with 0.362 kg of water, passed through a suitable perforated disk granulating unit so that rough granules are obtained having a rod diameter of about 1.5 mm and a rod length of about 4–15 mm. The rough granules are rounded and dried.

(b)

0.300 kg of pellets, produced according to Example 4(a) are sprayed with a solution of 0.015 kg of "Eudragit"-RL and
0.060 kg of "Eudragit"-RS in
0.998 kg of dichloromethane and
0.428 kg of isopropanol.

The spraying process is conducted by way of a fluidized-bed granulator.

Of the thus-produced pellets, a separated dose of 0.3 mg of iloprost is tested according to USP XXI in phosphate buffer solution, pH 7.5, for its in-vitro release rate, with the following result:

| Time (Hours) | Cumulative Release in % |
|---|---|
| 1 | 6.4 |
| 2 | 30.7 |
| 3 | 54.1 |
| 5 | 80.0 |
| 6 | 87.9 |

We claim:

1. A medicinal agent for sustained release of 4-(3-cyclopentyloxy-4-methoxyphenyl)-2-pyrrolidone or 5-{hexahydro-5-hydroxy-4-(3-hydroxy-4-methyl-1-octen-6-ynyl)-2(1H)-pentalenylidene}-pentanoic acid as an active compound, wherein the active compound is in the form of a solid which is poorly soluble in water, comprising a pellet, which comprises a pharmacologically acceptable auxiliary agent, in or on which pellet the active compound is distributed in a microcrystalline form or in molecular dispersion, said active compound-containing pellet being covered with a diffusion membrane, wherein the diffusion membrane comprises one or more of an acrylic acid ester, a methacrylic acid ester, a copolymer of one or more of an arcylic and one or more of a methacrylic acid ester, a vinyl acetate, or a modified cellulose derivative which retards permeability of the active compound, and wherein the pellet has an average diameter of 0.4–2.5 mm and the diffusion membrane has a thickness of 0.01–0.5 mm.

2. A medicinal agent for sustained release of 4-(3-cyclopentyloxy-4-methoxy-phenyl)-2-pyrrolidone or 5-{hexahydro-5-hydroxy-4-(3-hydroxy-4-methyl-1-octen-6-ynyl)-2(1H)-pentalenylidene}-pentanoicacid, a solid, poorly water-soluble active compound, comprising said active compound in the form of a molecular dispersion or in microcrystalline form on the surface of a pellet, which is comprised of an auxiliary agent and is devoid of active compound, or a microcrystalline active compound in admixture with an auxiliary agent, in the form of a pellet, wherein the resultant pellet has an average grain size of no more than 0.1 mm, and is covered with a diffusion membrane, wherein the diffusion membrane comprises one or more of an acrylic acid ester, a methacrylic acid ester, a copolymer of one or more of an acrylic and one or more of a methacrylic acid ester, a vinyl acetate, or a modified cellulose derivative which retards permeability of the active compound, and the diffusion membrane has a thickness of 0.01–0.5 mm, and wherein the active compound in or on said pellet exhibits a surface area value of at least 20,000 cm$^2$ per gram.

3. A medicinal agent according to claim 1, wherein the pellets have a core devoid of the active compound, the active compound being on the surface of the core in the form of a molecular dispersion or in microcrystalline form, with an average grain size of no more than 0.1 mm.

4. A medicinal agent according to claim 3, wherein the pellets devoid of active compound consist essentially of disaccharides and polysaccharides.

5. A medicinal agent according to claim 1, wherein the pellets consist essentially of a homogeneous mixture of disaccharides, polysaccharides, and microcrystalline active compound with an average grain size of maximally 0.1 mm.

6. A medicinal agent according to claim 1, wherein the covering membrane consists of an acrylic resin.

7. A medicinal agent according to claim 1, wherein the active agent is 4-(3-cyclopentyloxy-4-methoxyphenyl)-2-pyrrolidone.

8. A medicinal agent according to claim 7, wherein the membrane-covered pellets contain 0.5–5.0% by weight of active compound.

9. A medicinal agent according to claim 1, wherein the active agent is 5-{hexahydro-5-hydroxy-4-(3-hydroxy-4-methyl-1-octen-6-ynyl)-2(1H)-pentalenylidene}pentanoic acid.

10. A medicinal agent according to claim 9, wherein the membrane-covered pellets contain 0.2–0.5% by weight of active compound.

11. A medicinal agent according to claim 1, which are capsules containing respectively 0.1–100 mg of active compound.

* * * * *